United States Patent
Lockman

(10) Patent No.: US 11,565,251 B2
(45) Date of Patent: Jan. 31, 2023

(54) MICROFLUIDIC CHIP AS A MODEL FOR BLOOD-TISSUE BARRIERS

(71) Applicant: WEST VIRGINIA UNIVERSITY, Morgantown, WV (US)

(72) Inventor: Paul Lockman, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 543 days.

(21) Appl. No.: 16/786,335

(22) Filed: Feb. 10, 2020

(65) Prior Publication Data
US 2020/0254447 A1 Aug. 13, 2020

Related U.S. Application Data

(60) Provisional application No. 62/803,935, filed on Feb. 11, 2019.

(51) Int. Cl.
*B01L 3/00* (2006.01)
*C12M 3/06* (2006.01)

(52) U.S. Cl.
CPC ... *B01L 3/502707* (2013.01); *B01L 3/502715* (2013.01); *C12M 23/16* (2013.01); *B01L 2400/04* (2013.01)

(58) Field of Classification Search
CPC ......... B01L 3/502707; B01L 3/502715; B01L 2400/04; B01L 2300/0832; B01L 2300/0877; B01L 2400/0487; B01L 3/502761; C12M 23/16; C12M 25/02; C12M 35/08
See application file for complete search history.

(56) References Cited

U.S. PATENT DOCUMENTS

| 2005/0266582 | A1 | 12/2005 | Modlin et al. |
| 2009/0023608 | A1 | 1/2009 | Hung et al. |
| 2010/0216244 | A1 | 8/2010 | Wu et al. |
| 2015/0004077 | A1* | 1/2015 | Wikswo ................ C12M 29/10 422/502 |
| 2019/0093077 | A1* | 3/2019 | Hamilton ............. A61K 35/407 |

OTHER PUBLICATIONS

Lee et al. "A microfluidic platform for quantitative analysis of cancer angiogenesis and intravasation" Biomicrofluidics 8, 054102 (Year: 2014).*
Terrell-Hall, et al., "Permeability across a novel microfluidic blood-tumor barrier model", CNS, 14:3, 10 pages. (2017).

* cited by examiner

*Primary Examiner* — Samuel P Siefke
*Assistant Examiner* — Quocan B Vo
(74) *Attorney, Agent, or Firm* — Kramer & Amado, P.C.

(57) ABSTRACT

A microfluidic device is useful for modelling drug transmission across the vasculature and vascular barriers. The device includes a frame, a fluid-permeable lumen configured to carry a fluid through the frame in a first direction, a first chamber surrounding the lumen, and a second chamber surrounding the first fluid-permeable chamber. At least one surface of the first chamber is configured for deposition of a first population of endothelial cells. An outer surface of the second chamber is configured for deposition a second population of cells. The second chamber is configured to carry a fluid through the frame in a second direction. The fluid-permeable lumen is configured to allow the fluid to permeate through a wall of the lumen into the first chamber, and the first chamber and the second chamber are in fluid communication with each other.

20 Claims, 4 Drawing Sheets

MICROFLUIDIC CHIP AS A MODEL FOR BLOOD-TISSUE BARRIERS

TECHNICAL FIELD

Various embodiments disclosed herein relate generally to a multi-layer microfluidic chip that provides an in-vitro model of the blood brain barrier and the blood tumor barrier.

BACKGROUND

Understanding the blood-brain barrier (BBB) and blood-tumor barrier (BTB) and how they change in response to disease states is critical to developing effective therapeutic options to treat, for example, tumors of the CNS. Unfortunately, current in-vitro models for these vascular systems do not accurately represent physiological conditions, limiting the accuracy of testing different pharmacological agents.

Transwell plates are currently used to mimic the interaction between endothelial cells and surrounding systems. This method however is limited by its static nature. Transwell plates additionally lack the dimension of fluid flow, which limits physiologic relevance.

In an attempt to address this issue and provide a more realistic model, microfluidic chips have recently been developed which allow for fluid flow through the system and are of a more physiologically relevant size.

Although the use of microfluidics is an improvement from the static transwell plate method, there remains several limiting factors, making it an imperfect and difficult to interpret model. Due to the nature of the microfluidic chambers, establishing endothelial and other cell type colonies is very difficult and can take months to perfect. The sealed microfluidic system also makes the cells inaccessible for further research, thus limiting researchers from understanding how cells may react to different treatments. Additionally, unlike transwell plates, current microfluidic chips are single throughput systems, making it an unrealistic model for drug screenings which often require hundreds if not thousands of trials.

Furthermore, current microfluidic chambers are so small that they require a mold and the pouring of poly-di-methyl-siloxane into the mold. This material may bind certain drug types, which limits its use in drug discovery.

In order for researchers to develop a better understanding of the BBB and BTB under different disease states, it is critical that a physiologically relevant, easy to use, and reliable model be established which can be used for drug screening trials.

SUMMARY OF EXEMPLARY EMBODIMENTS

Various embodiments recite a microfluidic chip including a first layer, a second layer and a third layer, wherein each layer is removably attached to the other layers. The second layer includes a lumen, wherein the lumen contains one or more inlet ports, one or more outer compartments, one or more porous barrier layers, one or more central compartments, and one or more outlet ports.

Various embodiments recite a microfluidic chip wherein the second layer further contains a first chamber and a second chamber that are separated from each other and configured to culture one or more cell populations.

Various embodiments recite a microfluidic chip wherein the second layer may contain additional chambers configured to culture one or more cell populations.

Various embodiments recite a microfluidic chip wherein the one or more porous barrier layers contain pores with a size ranging from about 2 µm to about 3 µm.

Various embodiments recite a microfluidic chip wherein the one or more central compartments contain cells selected from the group consisting of brain cells and cancer cells.

Various embodiments recite a microfluidic chip wherein the chip is configured to allow for high throughput drug screening.

Various embodiments recite a microfluidic chip wherein the microfluidic chip is configured to allow for measurement of drug concentrations in multiple areas of the chip.

Various embodiments disclosed herein relate to a microfluidic device, including a frame, a first inlet port and a second inlet port within the frame, and a first exit port and a second exit port within the frame. A fluid-permeable lumen may extend from the first inlet port to the first exit port, with a fluid-permeable surface extending parallel to the lumen. A porous barrier layer may connect the fluid permeable surface to the frame. A removable top layer and a removable bottom layer may be removably connected to the frame. In various embodiments, the removable top and bottom layers may face opposing surfaces of the porous barrier layer. The bottom layer may have a channel therein. An outer surface of the lumen and a first surface of the fluid-permeable surface define a first chamber. A second surface of the fluid-permeable surface and the channel in the bottom layer may define a second chamber, where the second chamber extends from the second inlet port to the second exit port.

The fluid permeable surface parallel to the lumen may be configured for growth of a first population of cells thereon, where the first population of cells may be vascular endothelial cells or lymphatic endothelial cells. The channel in the bottom layer may have a surface configured for growth of a second population of cells thereon, where the second population of cells may be nerve cells, brain cells, muscle cells, tumor cells, or a combination thereof.

In various embodiments of the microfluidic device, the fluid-permeable lumen is configured to allow permeation of a fluid from a first fluid stream traveling through the lumen into the first chamber, and the fluid-permeable surface is configured to allow permeation of the fluid from the first chamber into a second fluid stream traveling through the second chamber. The lumen may be configured to allow a fluid from the first fluid stream to permeate into the first chamber to contact the first population of cells, and the fluid-permeable surface may be configured to allow permeation of the fluid from the first chamber into the second chamber to contact the second population of cells.

Various embodiments disclosed herein relate to a microfluidic device, including a frame, a first inlet port and a second inlet port within the frame, and a first exit port and a second exit port within the frame. A fluid-permeable lumen extends from the first inlet port to the first exit port, and a fluid-permeable surface extends parallel to the lumen. A porous barrier layer may connect the fluid permeable surface to the frame. The porous barrier layer may be a porous membrane with pores having a size of between about 2 and about 3 µm. The porous barrier layer may be a mesh layer with a mesh size of between 20 mesh and 2500 mesh.

The microfluidic device as disclosed herein is configured to allow for high throughput drug screening.

The current disclosure relates to a microfluidic device and a method of using the same, where the device may be used to model drug transport in a tissue, organ, or system. The device includes a frame; a fluid-permeable lumen configured to carry a fluid through the frame in a first direction; a first chamber surrounding the lumen, at least one surface of the first chamber configured for deposition of endothelial cells; and a second chamber surrounding the first fluid-permeable chamber. The second chamber may include an inner surface configured for deposition of cells, and may be configured to carry a fluid through the frame in a second direction. The fluid-permeable lumen may be configured to allow the fluid to permeate through a wall of the lumen into the first chamber, and the first chamber and the second chamber may be in fluid communication with each other. In various embodiments, the first direction of fluid flow through the lumen is the same as the second direction of fluid flow through the second chamber. Alternatively, the first direction of fluid flow may be opposite to the second direction of fluid flow.

In various embodiments of the microfluidic device, the first chamber has a fluid-permeable outer wall, and the first chamber and the second chamber are in fluid communication through the fluid-permeable outer wall of the first chamber. In various embodiments, the first chamber and the second chamber each contact a porous barrier layer connected with the frame, and the first chamber and the second chamber are in fluid communication through the porous barrier layer.

The microfluidic device may further include a top layer removably connected with the frame on an upper surface of the porous barrier layer, and a bottom layer removably connected with the frame on a lower surface of the porous barrier layer. A wall of the first chamber may be connected with the porous barrier layer, and a wall of the outer chamber is formed on at least one of an upper surface of the bottom layer, and a lower surface of the upper layer.

Various embodiments disclosed herein relate to a method of studying drug delivery through a cellular layer in a tissue, organ, or system, using a microfluidic device. The microfluidic device includes a frame; a fluid-permeable lumen configured to carry a fluid through the frame in a first direction; a first chamber surrounding the lumen, at least one surface of the first chamber configured for deposition of endothelial cells; and a second chamber surrounding the first fluid-permeable chamber. The second chamber may include an inner surface configured for deposition of cells, and may be configured to carry a fluid through the frame in a second direction. The fluid-permeable lumen may be configured to allow the fluid to permeate through a wall of the lumen into the first chamber, and the first chamber and the second chamber may be in fluid communication with each other. The method includes steps of:

- depositing a first population of endothelial cells on at least one surface of the first chamber;
- depositing a second population of cells on the inner surface of the second chamber;
- causing a first nutrient solution to flow through the fluid-permeable lumen and permeate through the wall of the lumen into the first chamber, wherein the first nutrient solution comprises a drug;
- causing a second nutrient solution to flow through the second chamber, wherein the first chamber and the second chamber are in fluid communication; and
- determining an extent of drug uptake by the second population of cells.

In various embodiments of the disclosed method, the first population of endothelial cells is a population of vascular endothelial cells, and the second population of cells is a population of brain cells, nerve, cells, tumor cells, pancreatic cells, or a combination thereof.

BRIEF DESCRIPTION OF THE DRAWINGS

In order to better understand various embodiments, reference is made to the accompanying drawings, wherein.

To facilitate understanding, identical reference numerals have been used to designate elements having substantially the same or similar structure or substantially the same or similar function.

DETAILED DESCRIPTION OF THE INVENTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or" refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

Figure 1:
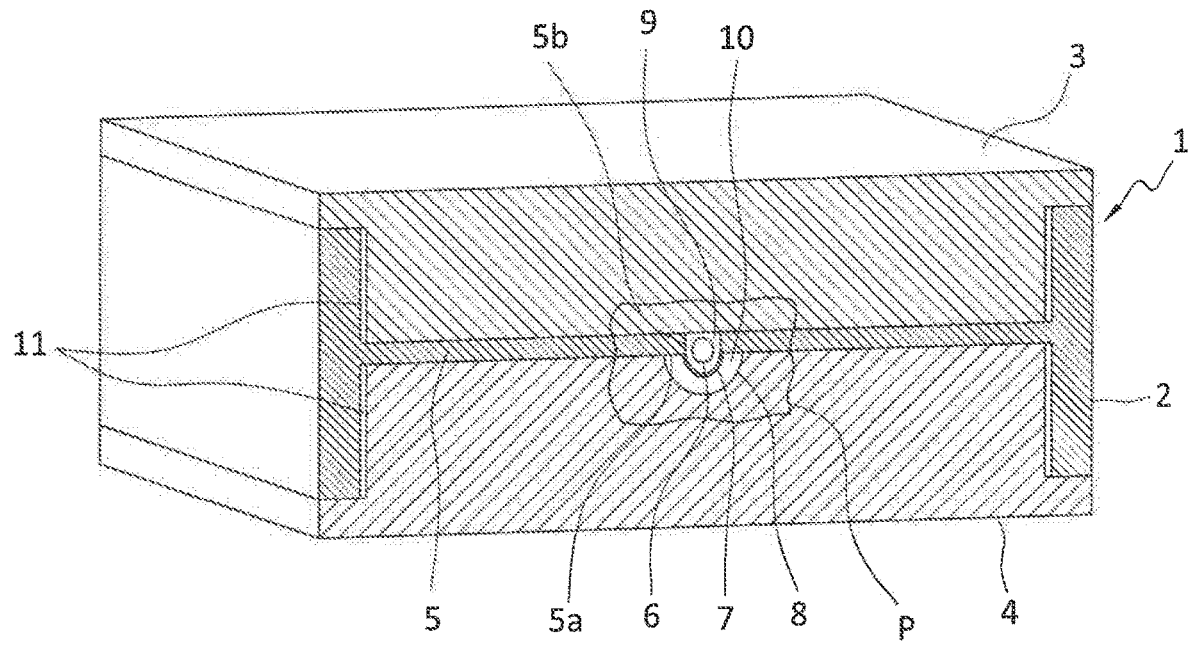
FIG. 1 illustrates a cross-sectional perspective view of the assembled microfluidic chip in the present embodiment.

FIG. 1 illustrates a cross section perspective view of the microfluidic chip 1 containing a top layer 3, a middle layer 5 and a bottom layer 4. Either the top layer 3 or the bottom layer 4 may include a first concave depression 8 configured to surround a lumen 6 that is longitudinally positioned in the middle layer 5. The middle layer 5 further includes a fluid-permeable surface 7 surrounding lumen 6 that extends longitudinally across layer 5. The top layer 3 and the bottom layer 4 are configured to mate with a frame 2 surrounding the middle layer 5.

Figure 2:
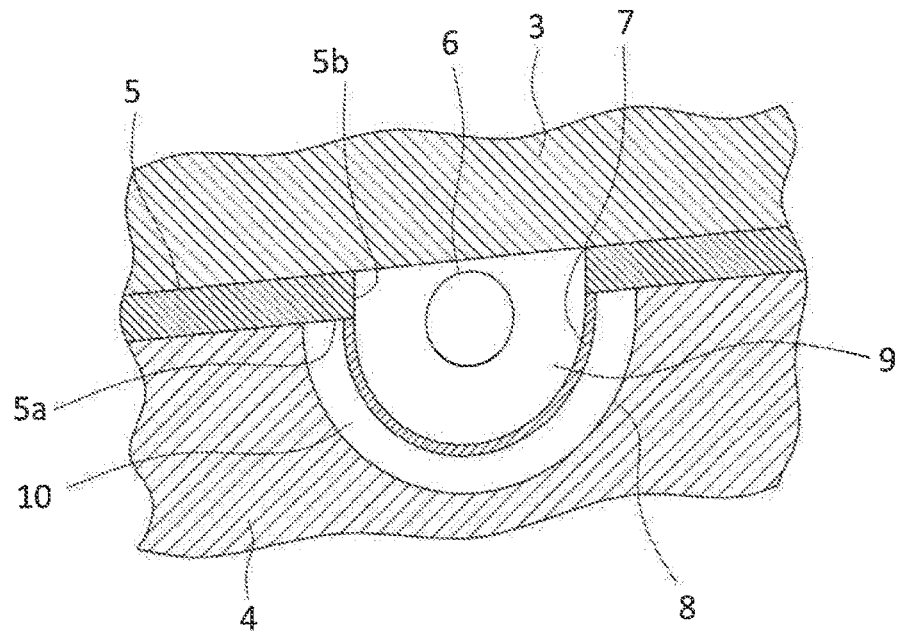
FIG. 2 illustrates a detail of the cross-sectional view of FIG. 1, where the boundary of the view of FIG. 2 is defined by line P in FIG. 1.

The microfluidic chip 1 of the invention combines the benefit of the high throughput nature of transwell plates, with the physiological relevance of microfluidic channels. As seen in FIG. 1 and in the cross section detail view of FIG. 2 (where the boundary of the view of FIG. 2 is defined by line P in FIG. 1), the microfluidic chip 1 may include a top layer 3, a porous barrier layer 5 connected to a frame 2, and a bottom layer 4, each layer removably attached to the other layers. Top and bottom layers 3 and 4 may removably engage frame 2, with a water-impermeable seal layer 11 therebetween. In various embodiments, there is a longitudinal slit with edges 5b in the porous barrier layer 5. A lumen 6 having a fluid-permeable wall occupies a space defined by the longitudinal slit in the permeable layer. A fluid-permeable surface 7 extending parallel to the lumen 6 may be connected to edges 5b of the slit in the porous barrier layer 5. The fluid-permeable surface 7 may be planar or non-planar. The permeable surface 7 may have the shape of a concave depression, relative to the porous barrier layer 5. In some embodiments, the fluid-permeable surface 7 is semi-cylindrical and surrounds lumen 6, as shown in FIG. 1. A space between an inner surface of fluid-permeable surface 7 and lumen 6 defines a first chamber 9 surrounding lumen 6.

The bottom layer 4 includes a channel 8 in a surface thereof. When bottom layer 4 and top layer 3 are positioned in frame 4 adjacent to barrier layer 5, an outer surface of the fluid-permeable surface 7 and the inner surface of channel 8 define a second chamber 10, adjacent to the first chamber 9. Where the surface 7 is in the shape of a concave depression, relative to barrier layer 5, the second chamber 10 may surround the first chamber 9, as shown in FIG. 2. The first and second chambers are in fluid communication with each other. In various embodiments, the first and second chambers due to permeation of fluid from the first chamber to the second chamber through fluid-permeable surface 7. Additionally, the first chamber 9 may contact edges 5b of porous barrier layer 5, while the second chamber 10 may contact a lower edge surface 5a of porous barrier layer 5. Therefore, the first and second chambers 9 and 10 may be in fluid communication through porous barrier layer 5. Further, the first chamber 9 is in fluid communication with the interior of lumen 6, due to permeation of fluid through the wall of lumen 6.

In various embodiments, the porous barrier layer may be a porous membrane with pores having a size of between about 1 and about 10 µm, about 1.5 and about 5 µm, or about 2 and about 3 µm. Alternatively, the porous barrier layer may be a mesh layer with a mesh size of between 18 mesh and 835 mesh, 25 mesh and 400 mesh, 35 mesh and 200 mesh, or 50 mesh and 120 mesh.

In various embodiments, at least one surface of the first chamber inner chamber 9 is configured for deposition of a first population of endothelial cells thereon. The cells may be deposited on an inner surface or an outer surface of fluid-permeable surface 7. Endothelial cells, such as vascular or lymphatic endothelial cells, may be deposited on fluid-permeable surface 7, allowing surface 7 to serve as a model for a blood vessel or lymph vessel. Similarly, the outer surface of the second chamber 10 may be configured for deposition of cells thereon. Chamber 10 may have a surface configured for growth of a second population of cells selected from the group consisting of nerve cells, brain cells, muscle cells, or tumor cells thereon. Since fluid permeates from the interior of chamber 9 through endothelial cells on surface 7 into chamber 10, the second population of cells in chamber 10 may serve as a model for tissues served by a blood or lymph vessel.

In various embodiments, the lumen 125 may have a diameter which corresponds to the diameter of a desired blood vessel. The lumen may have a diameter of about 1 mm to about 10 mm, 1 mm to 7 mm, 1.5 mm to 6 mm, or 2 mm to 5 mm.

Lumen 6 is configured to allow a first fluid to flow therethrough in a first direction, while chamber 10 is configured to allow a second fluid to flow therethrough in a second direction. The first and second direction may be parallel to each other, or opposite to each other. Chamber 9 is may contain fluid due to permeation of fluid into chamber 9 from lumen 6 and from chamber 10.

Figure 3:
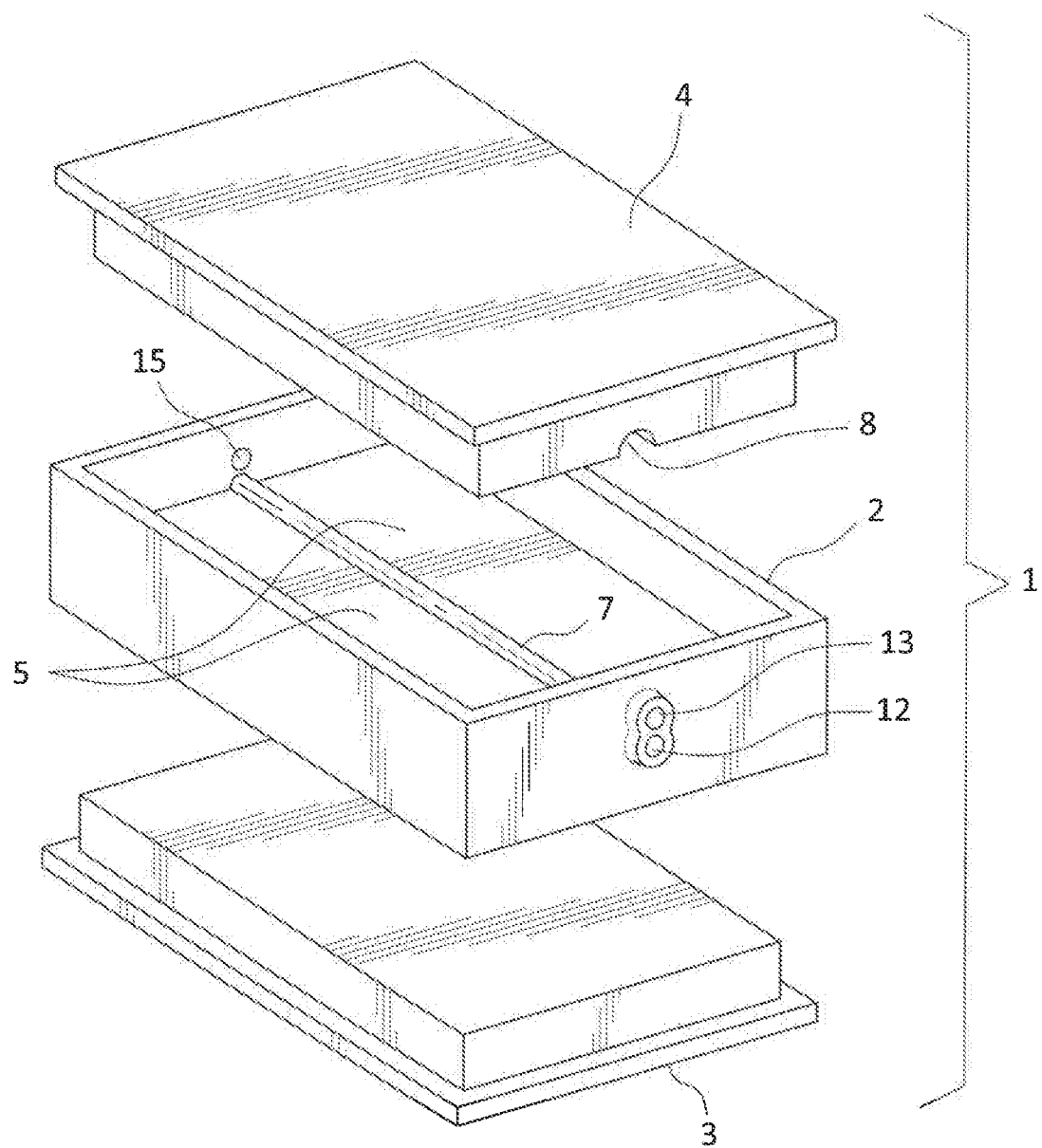
FIG. 3 illustrates an exploded perspective view of the microfluidic chip in the present embodiment.

FIG. 3 illustrates an exploded perspective view of the microfluidic chip 300, which includes the top layer 3, the porous barrier layer 5 connected to frame 2, and the bottom layer 4. Fluid-permeable surface 7 is connected to the porous barrier layer 5. When bottom layer 4 is attached to frame 2, the inner surface of channel 8 and an outer layer of fluid-permeable surface 7 define outer chamber 10. As shown in FIG. 1, a first inlet port 12 conveys fluid into lumen 6, as shown in FIG. 1. An outlet port 14, shown in FIG. 4, conveys fluid out of lumen 6. Ports 13 and 15 are configured to allow fluid flow through outer chamber 10, as shown in FIG. 1. Port 13 may serve as an inlet port or as an outlet port, depending on whether a user wishes fluid flowing through outer chamber 10 to flow in the same direction as fluid flowing through lumen 9, or in the opposite direction to fluid flowing through lumen 9.

Figure 4:
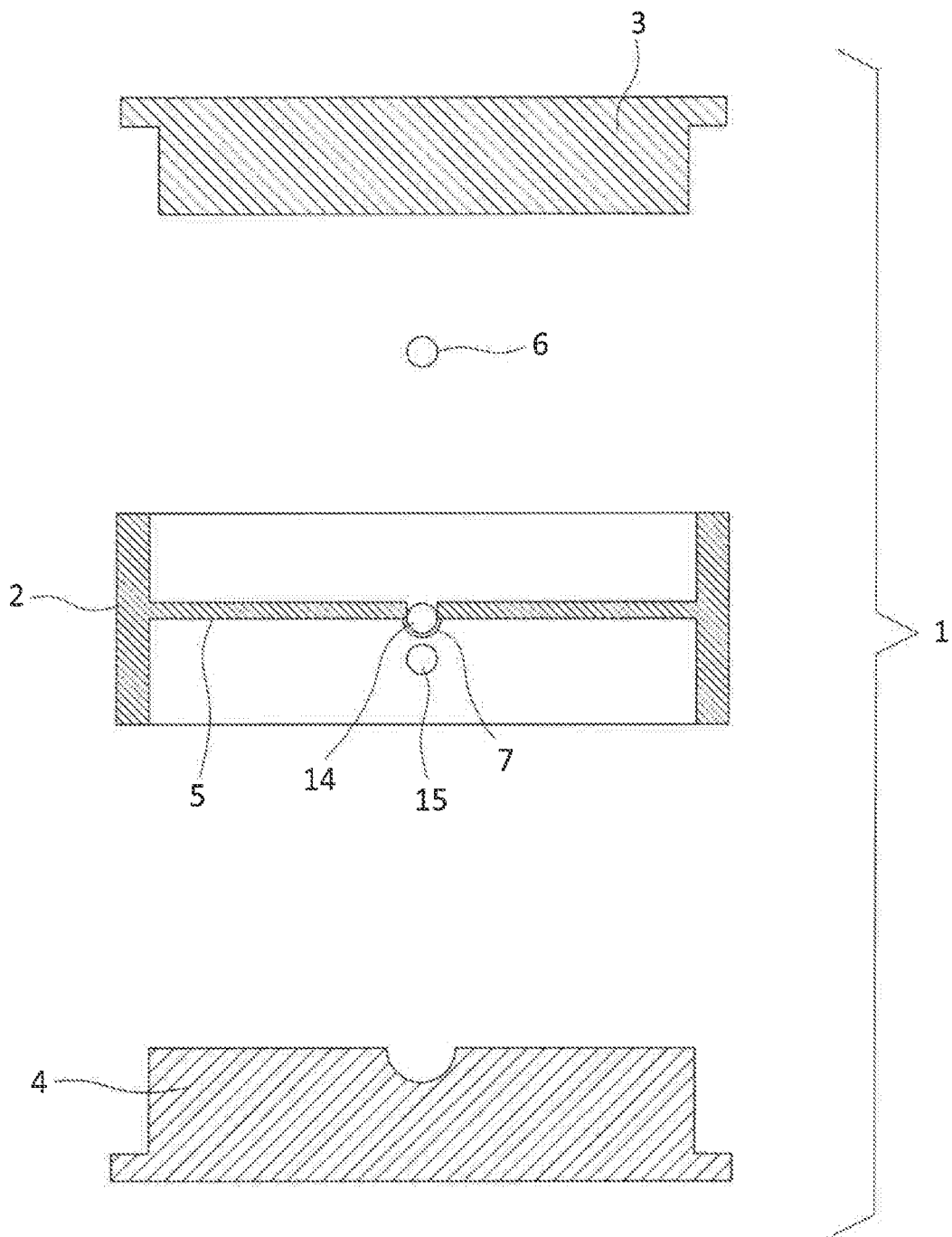
FIG. 4 illustrates a cross-sectional exploded side view of the microfluidic chip in the present embodiment.

FIG. 4 shows an exploded cross section view of microfluidic device 1, including the top layer 3, the porous barrier layer 5 connected to frame 2, and the bottom layer 4. Fluid-permeable surface 7 is connected to the porous barrier layer 5. Lumen 6 is positioned parallel to fluid permeable surface 7, and is connected to inlet port 12, shown in FIG. 3, and outlet port 14. When bottom layer 4 is attached to frame 2, the inner surface of channel 8 and an outer layer of fluid-permeable surface 7 define outer chamber 10. Port 15 allows fluid flow into or out of chamber 10.

In various embodiments, the microfluidic chip 1 may be fabricated from inorganic, polymeric or paper materials. Suitable inorganic materials may include, but are not limited to, silicon, glass, or ceramic materials. Suitable polymers include, but are not limited to, elastomers, thermoset polyester, thermoplastic polymers, polystyrene, polycarbonate, acrylic materials, perfluorinated compounds (PFEP/PFA/PFPE), and polyurethane. Other suitable materials include hydrogels, and composite materials including cyclic-olefin copolymer (COC), and paper/polymer hybrid materials.

Various embodiments disclosed herein are directed to a method of studying drug delivery through an endothelial layer using the device of FIG. 1. The method includes the steps of:

depositing a first population of endothelial cells on at least one surface of the first chamber 9, which may be an inner or outer surface of fluid permeable surface 7;

depositing a second population of cells on the inner surface of the second chamber, by depositing the cells on the surface of channel 8;

causing a first nutrient solution to flow through the fluid-permeable lumen 6 and permeate through the wall of the lumen 6 into first chamber 9, where the first nutrient solution comprises a drug;

causing a second nutrient solution to flow through the second chamber 10, where the first chamber and the second chamber are in fluid communication; and determining an extent of drug uptake by the second population of cells.

In various embodiments of the disclosed method, the first population of endothelial cells is a population of vascular or lymphatic endothelial cells, and the second population of cells is a population of brain cells, nerve, cells, tumor cells, or a combination thereof. The microfluidic device provides a model for permeation of a drug or other solute from a biological fluid, e.g., blood, to a tissue, where a layer formed from the first population of endothelial cells serves as a model for a blood vessel wall.

The first population of endothelial cells may be deposited on fluid-permeable surface 7, where fluid permeable surface 7 has a porosity designed to mimic the porosity of a desired tissue, e.g., a blood vessel. The permeability of the surface 7 may be adjusted to model transmission through a cellular layer of a particular drug. The circulatory system includes:

blood vessels with a generally continuous cellular layer over a basement membrane;

fenestrated blood vessels having pores of a size ranging from 50 nm to 100 nm, over a basement membrane; and sinusoidal blood vessels lacking a basement membrane, having pores with a diameter of 7.5 µm-25 µm.

In various embodiments, blood vessels with a generally continuous cellular layer may be modeled by deposition of vascular endothelial cells on fluid permeable surface 7, where surface 7 includes pores having a size of less than 50 nm, e.g., 5 to 40 nm. Such a model is useful for modeling transmission of small molecule drugs.

Fenestrated blood vessels may be modeled by deposition of vascular endothelial cells on fluid permeable surface 7, where surface 7 includes pores having a size of 50 nm to 200 nm.

Sinusoidal blood vessels may be modeled by deposition of vascular endothelial cells on fluid permeable surface 7, where surface 7 has pores with a diameter of 5 μm-50 μm. Such a model is useful for modeling transmission of proteins, viruses, and/or cells.

In various embodiments, the microfluidic chip 1 may be configured to provide a model of the blood-brain barrier and blood-tumor-barrier that accurately represents the physiology of the vascular system. Referring to FIG. 2, a layer of cells, e.g., endothelial cells, e.g., vascular endothelial cells, deposited on the fluid permeable surface 7 serves as the model of the wall of a blood vessel. A nutrient solution flowing through permeable lumen 6 may serve as a model of blood flow through the system. The nutrient solution may contain a drug, and the drug-containing solution may permeate through the wall of lumen 6 into chamber 9, contacting the layer of endothelial cells on surface 7. The endothelial cells on surface 7 may undergo drug transport into the endothelial cells. Also, the endothelial cells on surface 7 may allow drug transport through the endothelial cell layer, due to permeation of fluid across surface 7 between chamber 9 and chamber 10. Brain, nerve, or tumor cells may be deposited on the outer wall 8 of chamber 10. Permeation of the drug-containing nutrient solution into chamber 10 allows uptake of the drug by the cells on wall 8 of chamber 10.

The top layer 3 and the bottom layer 4 may be separated from porous barrier layer 5. Endothelial cells on fluid permeable surface 7 and brain, nerve, or tumor cells on the outer wall 8 may then be recovered, and examined for the presence of drug. If the drug is found in the endothelial cells on surface 7, cellular uptake by the endothelial cells has occurred. If the drug is found in the brain, nerve, or tumor cells on wall 8, cellular uptake by these cells has occurred after transmission of the drug across the layer of endothelial cells. This may allow conclusions as to the efficacy of drug transport across the blood-brain barrier or blood-tumor barrier.

In various embodiments, the drug may be a hydrophobic synthetic drug, a hydrophilic synthetic drug, a natural product, an oligopeptide, a globular protein, or an enzyme. In some embodiments, the drug may be a genetically engineered virus or bacterial cell.

While the above discussion focuses on modeling transport between a blood vessel and an adjacent tissue layer (the blood-tissue barrier), transport between any pair of adjacent tissue layers may be modeled, if desired. The microfluidic chip 1 may be used to model drug transport within a variety of tissues, organs, or systems. For example, drug transport between layers in a blood vessel may be modeled by:

depositing a single layer of squamous endothelial cells on surface 7, to model the inner tunica intima layer of a blood vessel, and depositing layers of smooth muscle cells on the surface of channel 8, to model the tunica media layer of a blood vessel.

Transmission of a drug through the layer of squamous endothelial cells on surface 7 to the smooth muscle cells on the surface of channel 8 indicates that the drug is able to permeate through the wall of the blood vessel.

In addition to modeling drug transmission across the blood-brain barrier, transport between a pair of adjacent brain or nervous tissue layers may be modeled. Fluid flowing through chamber 10 may be used to model intercellular fluids and/or cerebrospinal fluid. A layer of white brain cells may be deposited on one of surface 7 and the surface of channel 8, while a layer of grey cells or a layer of nerve cells may be deposited on the other of these surfaces. The system may then be used to model drug transmission between adjacent brain tissue layers. Alternatively, layer of normal brain cells may be deposited on surface 7, while a layer of brain tumor cells may be deposited the surface of channel 8. In some embodiments, a drug-containing solution may flow through chamber 10, and the relative rate of drug uptake by normal brain cells and brain tumor cells may be determined. Alternatively, after allowing a nutrient-containing solution to flow through chamber 10, transport of cancer-associated peptides or other compounds from brain tumor cells to normal brain cells may be detected by identifying such compounds in normal brain cells on surface 7.

A variety of other tissue vascular flow/or physiologic process may be modeled. Transmission of a drug or a drug byproduct from the bloodstream into the liver may be modeled by depositing vascular endothelial cells on fluid permeable surface 7 and depositing liver cells, e.g., a layer of parenchymal hepatocytes, on the surface of channel 8, A nutrient solution flowing through lumen 6 may contain the drug and or its metabolite. Filtration of the drug or byproduct from the nutrient solution may be assessed by:

detecting a change in a concentration of the drug or byproduct in the nutrient solution as the nutrient solution flows past the parenchymal hepatocyte layer; and/or detecting the drug and or metabolite or the byproduct in the cells of parenchymal hepatocyte layer.

In some embodiments, drug transmission between adjacent liver tissues, e.g., a layer of parenchymal hepatocytes and a population of hepatic stellate cells or intrahepatic lymphocytes, may be modeled. In such cases, the layer of parenchymal hepatocytes may be deposited on surface 7, and a layer of normal or diseased hepatic stellate cells or intrahepatic lymphocytes may be deposited on the surface of channel 8. Drug transmission between normal and cancerous liver tissue may also be modeled.

Drug transport between a blood vessel and any of a variety of kidney cell types may be modeled. Also, drug transport between adjacent kidney cell types may be modeled, where the various kidney cell types may include kidney glomerulus parietal cells, kidney glomerulus podocytes and/or interstitial kidney cells. Drug transport between clear cell renal cell carcinoma cells and normal kidney cells may be modeled.

The pancreas is of particular interest. The pancreas contains cells arranged in lobes that have thin fibrous walls. The pancreas also contains pancreatic islets, which each contain alpha cells, beta cells, delta cells, and PP cells, each of which releases a different hormone. Due to its complicated structure, modeling drug transport in the pancreas is difficult. The microfluidic chip 1 allows modeling of drug or hormone transmission between blood vessels and cells in the pancreatic islets, where a layer of vascular endothelial cells on surface 7 may be used to model a blood vessel wall, and alpha cells, beta cells, delta cells, PP cells, or a mixture of islet cells may be deposited in channel 8 and used to model pancreatic tissue. Alternatively, transport of compounds between different pancreatic cellular types may be modeled by depositing, e.g., pancreatic alpha cells on surface 7 and pancreatic beta cells in channel 8.

Similar uses involving lung cells, smooth and/or striated muscle cells, endothelial cells from the digestive system, e.g., the intestines, and skeletal cells may be contemplated.

In various embodiments, the microfluidic chip 1 may be configured to allow for multiple replicates of a study to be run simultaneously, resulting in faster experimentation and a greater number of simultaneous drug screenings. This may be useful for the pharmaceutical industry where a large number of drug candidates and concentrations are needed to be tested in a short period of time. In one embodiment, the microfluidic chip 1 of the invention may be configured to allow for higher throughput models, which allows for a greater number of drugs to be screened against different disease states.

In some embodiments, the microfluidic chip 1 may be configured to allow testing of drug concentrations to take place in multiple chambers, i.e. inside an endothelial compartment, between the endothelial cells and adjacent compartments, and outside vascular network. This allows for drug uptake and movement to be more closely studied. This may also improve understanding of how cell populations and disease states affect transport of different drug types.

Figure 5A:
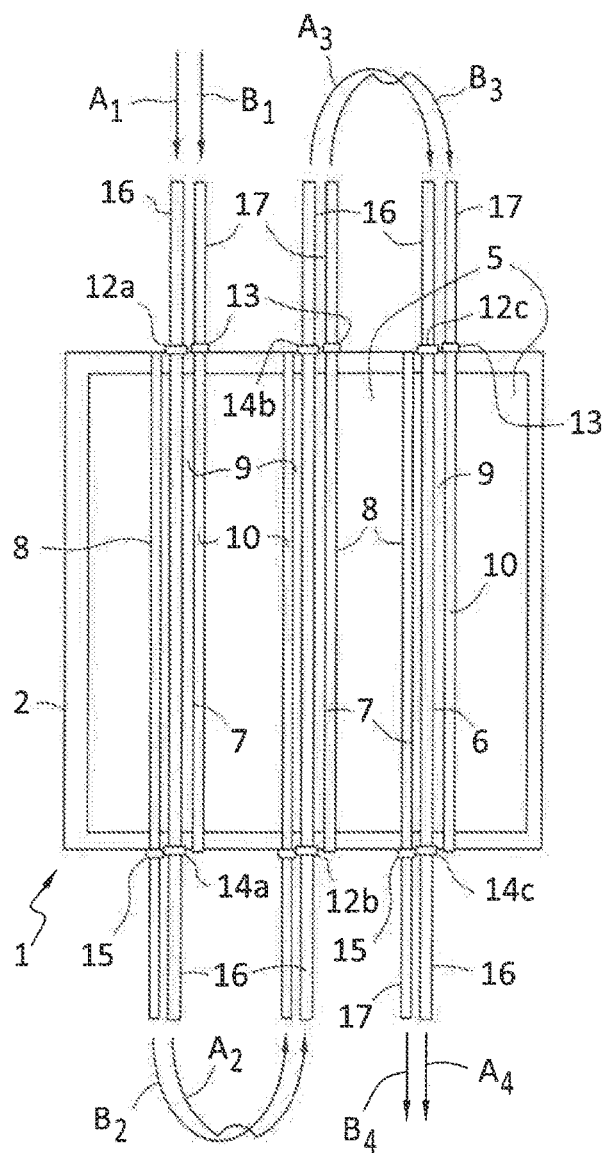
FIGS. 5A and 5B show views of the microfluidic chip of FIG. 1, illustrating fluid flow through the microfluidic chip.

FIG. 5A shows an embodiment of a microfluidic chip 1 adapted to allow sequential exposure of multiple cell populations to a single nutrient solution containing a desired drug. As shown in FIG. 5A, chip 1 has multiple walls 8 surrounding multiple fluid permeable surfaces 7. A layer of endothelial cells, e.g., vascular endothelial cells, may be deposited on each fluid permeable surface 7.

A lumen 6 is positioned adjacent to each fluid permeable surface 7. As seen in FIG. 5A, a nutrient fluid may flow into a first lumen 6 in the direction of arrow $A_1$ through port 12a. Tubes 16 allow entry of the nutrient fluid into lumens 6. The fluid may then exit the first lumen 6 through port 14a, and flow in the direction of arrow $A_2$ into a second lumen 6 through port 12b. The nutrient fluid then:

flows out of the second lumen 6 through port 14b in the direction of arrow $A_3$;
enters a third lumen 6 through port 12c; and
exits the third lumen 6 in the direction of arrow $A_4$ through port 14c.

A population of cells, which may be brain cells, nerve cells, or tumor cells, may be individually deposited on each wall 8. In various embodiments, an identical cell population may be deposited on each wall 8. In some embodiments, each wall 8 may have a different cell population, or two walls 8 may have a first population of cells and a third wall 8 may have a second population of cells. For example, a layer of healthy brain cells may be deposited adjacent to the first and third lumens 6 on wall 8, while a layer of brain tumor cells may be deposited adjacent to the second lumen 6 on wall 8. This allows the user to model drug transport from a drug-containing nutrient solution as it sequentially passes a layer of healthy brain cells, a layer of brain tumor cells, and a second layer of healthy brain cells. As another example, a layer of pancreatic alpha cells may be deposited adjacent to the first lumen 6 on wall 8, with a layer of pancreatic beta cells adjacent to the second lumen 6 and a layer of pancreatic PP cells adjacent to the third lumen 6.

A second nutrient fluid may flow into a chamber 10 between fluid permeable surface 7 and wall 8 in the direction of arrow B1. Tubes 17 allow flow of the second nutrient fluid to chambers 10, while ports 13 and 15 each allow the second nutrient fluid entry into, or exit from, a chamber 10, as desired. The second nutrient fluid may sequentially flow through each chamber 10, in the directions of arrows $B_1$ to $B_4$. The second nutrient fluid may flow in the same direction as the first nutrient fluid, as shown in FIG. 5A, or in an opposite direction to the first nutrient fluid.

Figure 5B:
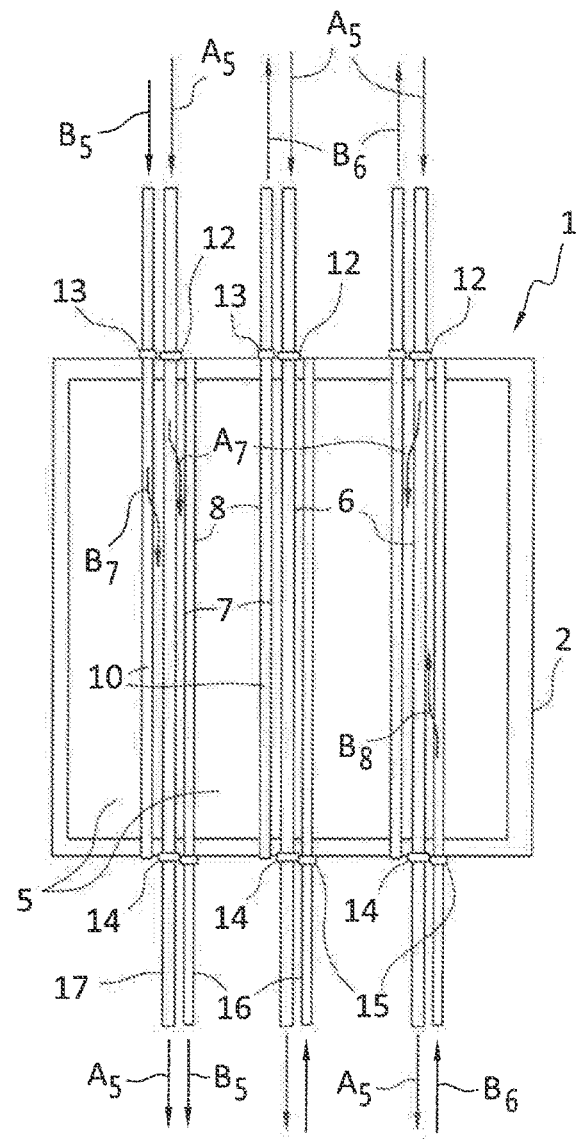

FIG. 5B shows an embodiment of a microfluidic chip 1 adapted to allow parallel simultaneous exposure of multiple cell populations to a single nutrient solution containing a desired drug. Structurally, the microfluidic chip 1 of FIG. 5B is similar to that of FIG. 5A, except that the direction of fluid flow is different. In each lumen 6, a nutrient fluid enters through a port 12 and exits through a port 14, traveling in the direction of arrow $A_5$. In each chamber 10, a second nutrient fluid travels through the chamber. As seen in FIG. 5B, the second nutrient fluid may travel in the direction of arrow $B_5$, in the same direction as the first nutrient solution. Alternatively, the second nutrient fluid may travel in the direction of arrow $B_6$, opposite to the first nutrient solution. The second nutrient fluid enters and/or exits chamber 10 through ports 13 and 15. Fluid traveling through lumen 6 may permeate into chamber 9 through the wall of lumen 6 in the direction of arrow $A_7$. Fluid traveling through chamber 10 may permeate into chamber 9 through surface 7 in the direction of arrow $B_7$ or $B_8$, depending on whether the nutrient fluid in lumen 6 and second nutrient fluid are travelling in the same direction or opposite directions.

In the embodiment of FIG. 5B, identical populations of cells may be deposited on each surface 8, and each lumen 6 may carry a nutrient solution with a different drug, allowing simultaneous modeling of drug transmission across the blood-tissue barrier for multiple active agents.

Although the embodiments of FIGS. 5A and 5B show three inner chambers 9 each having a first width and outer three outer chambers 10 each having a second width, with all lumens having the same diameter, this is not required. For example, referring to FIG. 5A, fluid flow enters a first lumen 6 through port 12a, and enters a third lumen through port 12c. In between, fluid flows from port 12b to port 14b through a second lumen. In various embodiments, the first and third lumens 6 may have a diameter of 6 mm to 10 mm, from 7 mm to 10 mm, or from 7.5 mm to 9 mm. The second lumen may have a diameter of 1 mm to 5 mm, from 1 mm to 4 mm, or from 1.5 to 3 mm. Each fluid permeable surface 7 may be sized so that an inner surface of each fluid permeable surface 7 is spaced from the corresponding lumen 6 by a distance of 0.5 mm to 3 mm, from 0.75 to 2 mm, or from 1 to 2 mm. The surface of each channel 8 may be sized so that an outer surface of each fluid permeable surface 7 is spaced from the corresponding channel 8 by a distance of 0.5 mm to 3 mm, from 0.75 to 2 mm, or from 1 to 2 mm. Due to the decreased diameter of the second lumen 6, the pressure and/or velocity of fluid flow is higher within the second lumen 6 than in the first and third lumens 6, allowing the device of FIG. 5A to be used to model the effect of changing blood vessel diameter on drug transmission through an endothelial cell layer on fluid permeable surface 7 to a layer of cells on wall 8. In the device of FIG. 5A, changes in fluid pressure and/or fluid velocity are a result of changing lumen diameter within a single fluid flow path.

Referring now to the device of FIG. 5B, lumens 6 may each have the same diameter or a different diameter. Additionally, the flow rate of a drug-containing fluid into each lumen 6 in the direction of arrows $A_5$ may be individually controlled by a pump or pumps. This allows the rate of fluid flow and/or fluid pressure to be individually controlled, so that the influence of blood flow rate and/or blood pressure on drug transmission through an endothelial cell layer on fluid permeable surface 7 may be modelled. Altering the direction and/or rate of fluid flow through outer chamber 10 may also allow the impact of blood flow rate to be modelled. For example, FIG. 5B shows a first lane where fluid flows through lumen 6 in the direction of arrow $A_5$, while fluid flows through chamber 10 in the direction of arrow $B_5$, where $A_5$ and $B_5$ are in the same direction. In such a case, blood moves in the direction of arrow C relative to fluid in chamber 10, where the magnitude of arrow C is the difference between the magnitudes of arrows $A_5$ and $B_5$. FIG. 5B shows second and third lanes where fluid flows through lumen 6 in the direction of arrow $A_5$, while fluid flows through lumen 6 in the direction of arrow $B_6$, where $A_5$ and $B_6$ are in opposite directions. Relative to fluid in chamber 10, countercurrent flow provides flow through lumen 6 the direction of arrow D, where the magnitude of arrow D is the sum of the magnitudes of arrows $A_5$ and $B_5$.

In the systems of FIG. 5A and or 5B, use of a pulsatile pump to drive fluid flow through lumens 6 may be used to simulate the pumping action of the heart on flow through lumens 6. The frequency of pulsations from the pump may be used to model the impact of a depressed or elevated heart rate on drug transmission. Changes in flow rate from the pump also allow modelling of changes in blood pressure and/or blood flow rate on drug transmission.

Alternatively, different populations of cells may be deposited on each surface 8, e.g., one surface 8 may contain tumor cells found in brain and a second surface 8 may contain healthy brain cells. Each lumen 6 may then carry a nutrient solution with the same drug, allowing simultaneous modeling of drug transmission of a single active agent across multiple distinct blood-tissue barriers.

Although the above discussion focuses on brain cells, nerve cells, and/or tumor cells, cells from a variety of tissues may be deposited in chamber 10, including normal or cancerous muscle cells, normal or cancerous liver cells, normal or cancerous lung cells, normal or cancerous kidney cells, and normal or cancerous pancreatic cells. This allows modeling of drug transmission across a variety of blood-tissue barriers. Other types of cells, including non-vascular endothelial cells, e.g., skin cells or cells lining the digestive tract; skeletal cells; stem cells; lung cells; fetal tissue cells; etc., may be deposited in chamber 10. The microfluidic chamber 1 may thus be used to model the blood-tissue barrier for a variety of biological tissues, organs, or systems.

Also, the above discussion focuses on deposition of vascular endothelial cells on surface 7. Lymphatic endothelial cells may be deposited on surface 7, allowing modeling of transmission of material across a lymph-tissue barrier.

Although the various embodiments have been described in detail with particular reference to certain aspects thereof, it should be understood that the invention is capable of other embodiments and its details are capable of modifications in various obvious respects. As is readily apparent to those skilled in the art, variations and modifications can be effected while remaining within the spirit and scope of the invention. Accordingly, the foregoing disclosure, description, and figures are for illustrative purposes only and do not in any way limit the invention, which is defined only by the claims.

What is claimed is:

1. A microfluidic device, comprising:
a frame;
a fluid-permeable lumen;
a fluid-permeable surface extending parallel to the lumen;
a porous barrier layer connecting the fluid permeable surface to the frame;
a top layer which is removably connected to the frame; and
a bottom layer having a channel, where the bottom layer is removably connected to the frame;
wherein:
an outer surface of the lumen and a first surface of the fluid-permeable surface define a first chamber,
a second surface of the fluid-permeable surface and the channel in the bottom layer define a second chamber.

2. The microfluidic device of claim 1, wherein the fluid-permeable lumen extends from a first inlet port to a first exit port; and
the second chamber extends from a second inlet port to a second exit port.

3. The microfluidic device of claim 1, wherein the fluid permeable surface is configured for growth of a first population of cells thereon.

4. The microfluidic device of claim 1, wherein the fluid permeable surface is configured for growth of a first population of vascular endothelial cells or lymphatic endothelial cells thereon.

5. The microfluidic device of claim 3, wherein the channel has a surface configured for growth of a second population of cells thereon, where the second population of cells is a population of cells from a biological tissue, organ, or system.

6. The microfluidic device of claim 3, wherein the channel has a surface configured for growth of a second population of cells selected from the group consisting of nerve cells, brain cells, muscle cells, or tumor cells thereon.

7. The device of claim 1, wherein:
the lumen is configured to allow permeation of a fluid from a first fluid stream traveling through the lumen into the first chamber; and
the fluid-permeable surface is configured to allow permeation of the fluid from the first chamber into a second fluid stream traveling through the second chamber.

8. The device of claim 3, wherein:
the lumen is configured to allow a fluid from a first fluid stream traveling through the lumen into the first chamber to contact the first population of cells; and
the fluid-permeable surface is configured to allow permeation of the fluid from the first chamber into the second chamber to contact a second population of cells lining the channel.

9. The device of claim 3, wherein:
the first population of cells is a population of vascular endothelial cells or lymphatic endothelial cells; and
the second population of cells is selected from the group consisting of nerve cells, brain cells, muscle cells, tumor cells, pancreatic cells, or a combination thereof.

10. The device of claim 1, wherein the porous barrier layer comprises a porous membrane with pores with a size of between about 2 and about 3 μm.

11. The device of claim 1, wherein the porous barrier layer comprises a mesh layer with a mesh size of between 20 mesh and 2500 mesh.

12. The device of claim 1, wherein the device is configured to allow for high throughput drug screening.

13. A microfluidic device for modeling drug transmission in a tissue, organ, or system, comprising:
a frame;
a fluid-permeable lumen configured to carry a fluid through the frame in a first direction;
a first chamber surrounding the lumen, at least one surface of the first chamber configured for deposition of a first population of cells;
a second chamber surrounding the first fluid-permeable chamber, wherein:

an inner surface of the second chamber is configured for deposition of a second population of cells; and the second chamber is configured to carry a fluid through the frame in a second direction;

wherein:

the fluid-permeable lumen is configured to allow the fluid to permeate through a wall of the lumen into the first chamber; and the first chamber and the second chamber are in fluid communication with each other.

14. The device of claim 13, wherein:

the first direction and the second direction are the same; or the first direction is opposite to the second direction.

15. The device of claim 13, wherein the first chamber has a fluid-permeable outer wall, and the first chamber and the second chamber are in fluid communication through the fluid-permeable outer wall of the first chamber.

16. The device of claim 13, wherein the first chamber and the second chamber each contact a porous barrier layer connected with the frame, and the first chamber and the second chamber are in fluid communication through the porous barrier layer.

17. The device of claim 16, further comprising a top layer removably connected with the frame on an upper surface of the porous barrier layer, and a bottom layer removably connected with the frame on a lower surface of the porous barrier layer.

18. The device of claim 17, wherein a wall of the first chamber is connected with the porous barrier layer, and a wall of the outer chamber is formed on at least one of:

an upper surface of the bottom layer; and a lower surface of the upper layer.

19. A method of studying drug delivery through a cellular layer in a tissue, organ, or system using the device of claim 13, comprising:

depositing the first population of cells on at least one surface of the first chamber;

depositing the second population of cells on the inner surface of the second chamber;

causing a first nutrient solution to flow through the fluid-permeable lumen and permeate through the wall of the lumen into the first chamber, wherein the first nutrient solution comprises a drug;

causing a second nutrient solution to flow through the second chamber, wherein the first chamber and the second chamber are in fluid communication; and determining an extent of drug uptake by the second population of cells.

20. The method of claim 19, wherein the first population of is a population of endothelial cells, and the second population of cells is a population of brain cells, nerve, cells, tumor cells, pancreatic cells, or a combination thereof.

* * * * *